US008830465B2

(12) United States Patent  
Taniguchi et al.

(10) Patent No.: US 8,830,465 B2  
(45) Date of Patent: Sep. 9, 2014

(54) DEFECT INSPECTING APPARATUS AND DEFECT INSPECTING METHOD

(75) Inventors: Atsushi Taniguchi, Fujisawa (JP); Yukihiro Shibata, Fujisawa (JP); Taketo Ueno, Kawasaki (JP); Shunichi Matsumoto, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 24 days.

(21) Appl. No.: 13/700,150

(22) PCT Filed: Jun. 17, 2011

(86) PCT No.: PCT/JP2011/003457  
§ 371 (c)(1),  
(2), (4) Date: Jan. 3, 2013

(87) PCT Pub. No.: WO2012/029222  
PCT Pub. Date: Mar. 8, 2012

(65) Prior Publication Data  
US 2013/0188184 A1  Jul. 25, 2013

(30) Foreign Application Priority Data

Aug. 30, 2010  (JP) ................................. 2010-191633

(51) Int. Cl.  
*G01J 4/00*  (2006.01)  
*G01N 21/956*  (2006.01)  
*G01N 21/95*  (2006.01)  
*G01N 21/94*  (2006.01)

(52) U.S. Cl.  
CPC .............. *G01N 21/956* (2013.01); *G01N 21/94* (2013.01); *G01N 21/9501* (2013.01)  
USPC ........................................................ 356/369

(58) Field of Classification Search  
CPC ....... G01J 4/00; G01N 21/956; G01N 21/211; G01N 2021/211

USPC .......................................................... 356/369  
See application file for complete search history.

(56) References Cited

U.S. PATENT DOCUMENTS 5,929,994 A * 7/1999 Lee et al. ...................... 356/364  
6,134,011 A * 10/2000 Klein et al. ................... 356/369

(Continued)

FOREIGN PATENT DOCUMENTS

JP  2005-147691  6/2005  
JP  2006-512588  4/2006

(Continued)

OTHER PUBLICATIONS

Office Action in corresponding Japanese Application No. JP 2010-191633, mailed Nov. 5, 2013, with partial English translation.

(Continued)

*Primary Examiner* — Roy M Punnoose  
(74) *Attorney, Agent, or Firm* — Antonelli, Terry, Stout & Kraus, LLP.

(57) ABSTRACT

A defect inspecting apparatus includes an irradiation optical system having a light source that emits illumination light and a polarization generation part that adjusts polarization state of the illumination light emitted from the light source, a detection optical system having a polarization analysis part that adjusts polarization state of scattered light from a sample irradiated by the irradiation optical system and a detection part that detects the scattered light adjusted by the polarization analysis part, and a signal processing system that processes the scattered light detected by the detection optical system to detect a defect presenting in the sample. The polarization generation part adjusts the polarization state of the illumination light emitted from the light source on the basis of predetermined illumination conditions and the polarization analysis part adjusts the polarization state of the illumination light emitted from the light source on the basis of predetermined detection conditions.

14 Claims, 9 Drawing Sheets

(56) References Cited

U.S. PATENT DOCUMENTS

| | | | |
|---|---|---|---|
| 6,307,627 B1 * | 10/2001 | Vurens | 356/369 |
| 6,515,745 B2 * | 2/2003 | Vurens et al. | 356/369 |
| 6,577,384 B2 * | 6/2003 | Wei et al. | 356/73 |
| 6,678,043 B1 * | 1/2004 | Vurens et al. | 356/237.2 |
| 7,295,305 B2 * | 11/2007 | Yoshida et al. | 356/237.5 |
| 8,681,328 B2 * | 3/2014 | Taniguchi et al. | 356/237.2 |
| 2002/0054290 A1 * | 5/2002 | Vurens et al. | 356/369 |
| 2004/0125375 A1 | 7/2004 | Some | |
| 2005/0062963 A1 * | 3/2005 | Yoshida et al. | 356/237.5 |
| 2007/0046931 A1 | 3/2007 | Oomori et al. | |
| 2007/0146706 A1 * | 6/2007 | Garcia-Caurel et al. | 356/369 |
| 2007/0171420 A1 * | 7/2007 | Ferrieu | 356/369 |
| 2008/0144024 A1 | 6/2008 | Nakano et al. | |
| 2009/0002695 A1 | 1/2009 | Saito et al. | |
| 2010/0014075 A1 | 1/2010 | Ueno et al. | |
| 2010/0182602 A1 | 7/2010 | Urano et al. | |
| 2010/0208249 A1 | 8/2010 | Shibata et al. | |
| 2011/0149275 A1 * | 6/2011 | Nakano et al. | 356/237.2 |
| 2013/0242294 A1 * | 9/2013 | Taniguchi et al. | 356/237.5 |

FOREIGN PATENT DOCUMENTS

| | | |
|---|---|---|
| JP | 2007-64948 | 3/2007 |
| JP | 2007-192759 | 8/2007 |
| JP | 2008-20374 | 1/2008 |
| JP | 2008-145399 | 6/2008 |
| JP | 2009-4610 | 1/2009 |
| JP | 2009-47429 | 3/2009 |
| JP | 2009-276273 | 11/2009 |
| JP | 2010-2406 | 1/2010 |
| JP | 2010-25713 | 2/2010 |
| JP | 2010/25713 | 2/2010 |
| JP | 2010-123182 | 6/2010 |

OTHER PUBLICATIONS

Office Action in corresponding Japanese Application No. JP 2010-191633, mailed Mar. 4, 2014, with partial English translation.

* cited by examiner

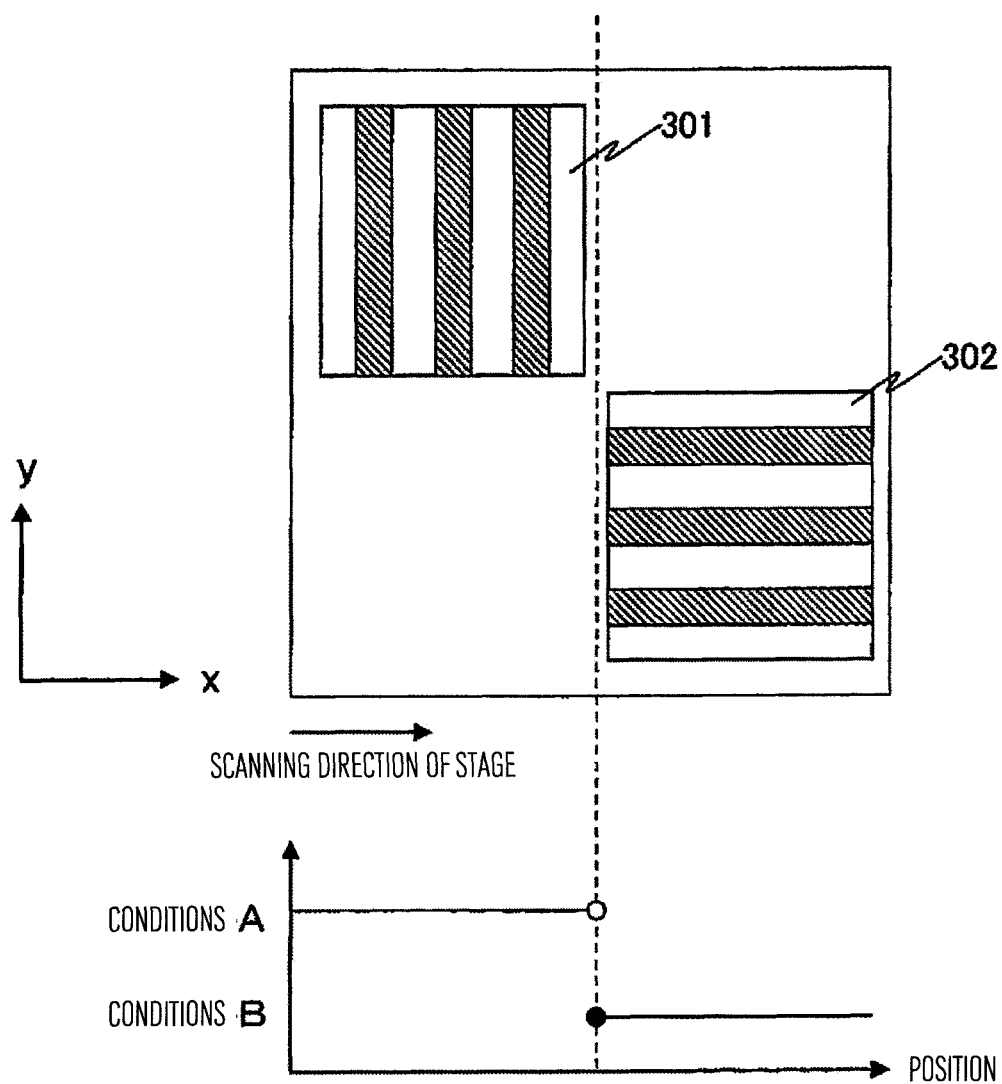

POLARIZATION GENERATOR

POLARIZATION ANALYZER

DEFECT INSPECTING APPARATUS AND DEFECT INSPECTING METHOD

TECHNICAL FIELD

The present invention relates to a defect inspecting apparatus and a defect inspecting method.

BACKGROUND ART

When an LSI and a liquid crystal board are manufactured, repeat patterns are sometimes formed on an object to be processed (e.g. semiconductor wafer). In such manufacturing of the LSI and the liquid crystal board, when a foreign matter adheres to the surface of the object to be processed or a defect is produced, failure such as, for example, insulation failure of wiring and a short circuit is caused. With recent miniaturization of circuit pattern, it is difficult to distinguish between the pattern formed on the object to be processed (indefective part) and a minute foreign matter or a defect.

Here, the defect is a particle adhered to a sample that is an object to be inspected, a crystal defect COP (Crystal Originated Particle) and a scratch produced by grinding.

With miniaturization of semiconductor devices, the size of a defect and a foreign matter on a minute pattern to be inspected is equal to or smaller than several ten nanometers. Since the size of the defect and the foreign matter to be inspected is small, reflected, diffracted and scattered light from the defect or the foreign matter is very weak and it is difficult to detect it by an optical method. Accordingly, conditions of illumination light for increasing the reflected, diffracted and scattered light from the defect or the foreign matter and conditions of detection thereof are groped. Particularly, in the sub-wavelength structure having semiconductor structure equal to about one tenth of wavelength, a semiconductor has structure birefringence and accordingly the polarization state of the reflected, diffracted and scattered light depends on the semiconductor structure strongly. A wire grid polarizer is a polarization element utilizing the polarization state of the sub-wavelength structure. Attention is paid to the polarization state of the sub-wavelength structure and there has been proposed a method in which the polarization state of incidence and detection is controlled to thereby reduce a signal from a semiconductor pattern and improve the detection sensitivity of defect.

Patent Literature 1 (JP-A-2006-512588 Publication) discloses "a system and a method of inspecting patterned and non-patterned object optically, comprising a step of deciding polarization shift introduced by the pattern and polarization of incident light beam subjected to the polarization shift by the pattern, a step of establishing the polarization state of the light beam in response to the decision and producing incident light beam impinging on the patterned object, a step of filtering reflected beam by polarization in response to the decision, and a step of generating a detection signal in response to detection of the filtered reflected light beam."

CITATION LIST

Patent Literature

Patent Literature 1: JP-A-2006-512588 Publication

SUMMARY OF INVENTION

Technical Problem

Patent Literature 1 discloses a bright-field inspection apparatus which irradiates the surface of an object to be inspected with illumination light and detects regular reflected light reflected from the surface of the object, although the Patent Literature 1 does not disclose the technique of detecting a defect or a foreign matter having the size equal to or smaller than several ten nanometers with high detection sensitivity in a dark-field inspection apparatus which detects light scattered from the surface of the object to be inspected and inspects a defect existing on the surface of the object.

In this patent application, there are provided a defect inspecting apparatus and a defect inspecting method of detecting scattered light from a more minute defect by suppressing scattered light from a repeat pattern part in a dark-field inspection apparatus suitable for inspection of an object to be inspected at high speed.

Solution to Problem

The outline of representatives of the present invention disclosed in this patent application is described briefly as follows:

(1) A defect inspecting apparatus comprises an irradiation optical system including a light source to emit illumination light and a polarization generation part to adjust polarization state of the illumination light emitted from the light source, a detection optical system including a polarization analysis part to adjust polarization state of scattered light from a sample irradiated by the irradiation optical system and a detection part to detect the scattered light adjusted by the polarization analysis part, and a signal processing system to process the scattered light detected by the detection optical system to detect a defect presenting in the sample. The polarization generation part adjusts the polarization state of the illumination light emitted from the light source on the basis of predetermined illumination conditions and the polarization analysis part adjusts the polarization state of the illumination light emitted from the light source on the basis of predetermined detection conditions. A defect inspecting apparatus comprises an irradiation step of adjusting polarization state of illumination light emitted and irradiating a sample to be inspected with the illumination light, a detection step of adjusting polarization state of scattered light from the sample irradiated in the irradiation step to be detected, and a signal processing step of processing the scattered light detected in the detection step and detecting a defect presenting in the sample. In the irradiation step, the polarization state of the illumination light emitted on the basis of predetermined illumination conditions are adjusted and in the detection step, the polarization state of the illumination light emitted on the basis of predetermined detection conditions are adjusted.

(2) A defect inspecting method comprises an irradiation step of adjusting polarization state of illumination light emitted and irradiating a sample to be inspected with the illumination light, a detection step of adjusting polarization state of scattered light from the sample irradiated in the irradiation step to be detected, and a signal processing step of processing the scattered light detected in the detection step and detecting a defect presenting in the sample. In the irradiation step, the polarization state of the illumination light emitted on the basis of predetermined illumination conditions are adjusted and in the detection step, the polarization state of the illumination light emitted on the basis of predetermined detection conditions are adjusted.

Advantageous Effects of Invention

There can be provided a defect inspecting apparatus and a defect inspecting method having improved detection sensitivity of a minute defect.

BRIEF DESCRIPTION OF DRAWINGS

FIG. 8 shows changing state of inspection conditions to circuit pattern form on a sample;

DESCRIPTION OF EMBODIMENTS

Embodiments of the present invention are now described.

A defect is a particle adhered to a sample that is an object to be inspected, a crystal defect COP (Crystal Originated Particle) and a scratch produced by grinding.

Embodiment 1

Referring now to FIGS. 1 to 8, the first embodiment of the optical inspection apparatus according to the present invention is described.

In the present invention, a foreign matter or a defect on a repeat pattern of sub-wavelength structure formed in a semiconductor wafer is an object. Typical repeat pattern contains long, narrow, parallel conductors or insulators and is generally named line and space pattern. The high-sensitive defect inspecting method utilizing structure birefringence of repeat pattern of the sub-wavelength structure is now described.

The following description is made by taking inspection using a dark-field inspection apparatus of a semiconductor wafer as an example.

Figure 1:
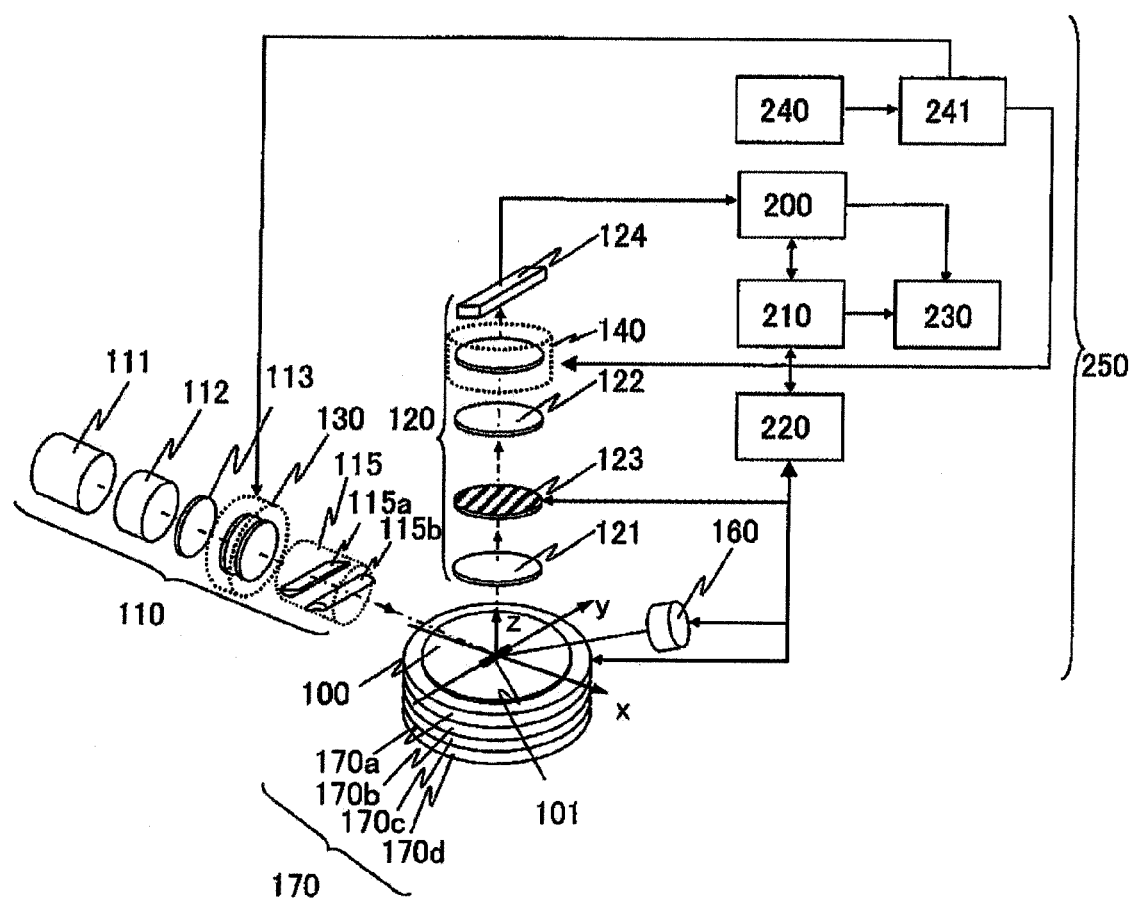
FIG. 1 is a diagram illustrating a first embodiment of an optical inspection apparatus according to the present invention.

FIG. 1 is a diagram illustrating the first embodiment of the optical inspection apparatus according to the present invention.

The optical inspection apparatus according to the embodiment 1 includes an illumination optical system 110, a stage part 170, a photographing optical system (detection optical system) 120 and a signal processing and control system 250. The illumination optical system 110 irradiates a sample that is an object to be inspected (semiconductor wafer) 100 with illumination light and scattered light from the irradiated semiconductor wafer 100 is detected by the detection optical system 120. At this time, the semiconductor wafer 100 is scanned by means of the stage part 170. The signal processing and control system 250 processes the scattered light from the semiconductor wafer 100 detected by the detection optical system 120 to detect a defect existing in the semiconductor wafer.

(Illumination Optical System 110)

The illumination optical system 110 includes a laser light source 111, attenuation filter 112, a beam expander 113, a polarization generation part 130 provided with a polarizing plate and a wave plate and a linear beam generation part 115 for irradiating the object to be inspected (semiconductor wafer) 100 with linear beam.

The laser light source 111 emits a laser beam. In this case, the light source 111 can utilize a gas laser, a semiconductor laser, a solid laser, a surface emitting laser or the like. Wavelength of infrared region, visible region and ultraviolet region can be used, although since optical resolution is improved as wavelength is shorter, light in ultraviolet region such as UV (Ultraviolet), DUV (Deep Ultraviolet), VUV (Vacuum Ultraviolet), EUV (Extreme Ultraviolet) and the like may be used when minute defect is viewed.

The attenuation filter 112 reduce the laser beam power emitted from the laser light source 111. When light emitted from the light source 111 is linear polarization, for example, the attenuation filter 112 may use an ND (Neutral Density) filter to adjust the intensity. The beam expander 113 expands a beam diameter of light.

The polarization generation part 130 includes a polarizing plate and a wave plate and adjusts the polarization state of light having the beam diameter expanded by the beam expander 113. The polarization state to be adjusted is decided on the basis of a control signal from a polarization condition control part 241 in the signal processing and control part described later. The polarization generation part 130 includes, for example, a ¼-wave plate and a ½-wave plate and adjusts a rotational angle of the ¼-wave plate and ½-wave plate in accordance with the polarization state decided on the basis of the control signal from the polarization condition control part 241.

Figure 3:
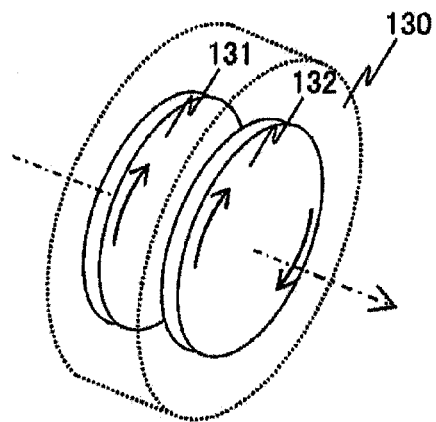
FIG. 3 is a schematic diagram illustrating a polarization generator of the first embodiment of the optical inspection apparatus according to the present invention.

FIG. 3 schematically illustrates the polarization generator 130 of the first embodiment of the optical inspection apparatus according to the present invention. The polarization generator 130 includes a ¼-wave plate 131 and a ½-wave plate 132. In this case, the order of the ¼-wave plate 131 and the ½-wave plate 132 may be reverse. The rotational angle of the ¼-wave plate 131 and the ½-wave plate 132 are set (rotation control) on the basis of the control signal from the polarization condition control part 241 shown in FIG. 1.

The linear beam generation part 115 receives light from the polarization generation part 130 having the adjusted polarization state to generate a linear beam. The linear beam generation part 115 is composed of lens group containing cylindrical lenses 115a and 115b, for example. At this time, the linear beam 101 is generated so that the longitudinal direction of the linear beam 101 is the direction y of the stage.

At this time, the polarization generation part 130 may be disposed behind the linear beam generation part 115. In this case, the semiconductor wafer 100 can be irradiated with the beam without producing shift in the beam subjected to polarization adjustment by the polarization generation part 130.

The linear beam 101 generated thus impinges on the surface of the semiconductor wafer 100 so that the direction y of the stage corresponds to the longitudinal direction of the linear beam 101.

(Detection Optical System 120)

The detection optical system 120 includes an object lens 121, a spatial filter 123, an image forming lens 122, a polarization analyzer 140 and a line sensor 124.

The object lens 121 concentrates light reflected, scattered and diffracted from the surface of the semiconductor wafer 100.

The spatial filter 123 shields part of the light reflected, scattered and diffracted from the surface of the semiconductor wafer 100 and concentrated by the object lens 121. The spatial filter 123 is disposed at a pupil position or at a position equivalent to the pupil position on the emission side of the object lens 121 and shields diffracted light by repeat pattern equal to or larger than the wavelength formed on the wafer 100.

The image forming lens 122 transmits scattered light which is not shielded by the spatial filter 123.

The polarization analyzer 140 includes a polarizing plate and a wave plate and adjusts the polarization state of scattered light transmitted by the image forming lens 122. The polarization state to be adjusted is decided, similarly to the polarization generation part 130, on the basis of the control signal from the polarization condition control part 241 in the signal processing and control part described later. The polarization generation part 140 includes, for example, a ¼-wave plate, a ½-wave plate and a polarizing plate and rotation of these components is controlled individually to adjust rotational angles of the ¼-wave plate, the ½-wave plate and the polarizing plate in accordance with the polarization state decided on the basis of the control signal from the polarization condition control part 241. Consequently, the polarization analyzer 140 can generate any incident polarization irrespective of the polarization state of incident light.

Figure 4:
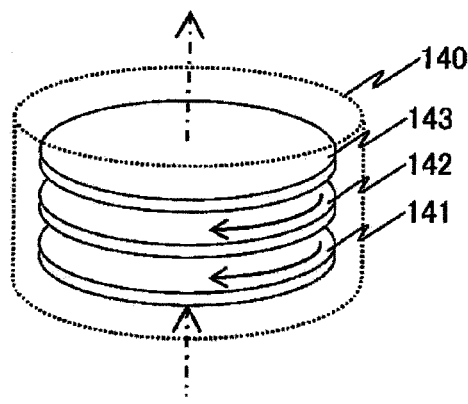
FIG. 4 is a schematic diagram illustrating a polarization analyzer of the first embodiment of the optical inspection apparatus according to the present invention.

FIG. 4 schematically illustrates the polarization analyzer 140 of the first embodiment of the optical inspection apparatus according to the present invention. The polarization analyzer 140 includes a ¼-wave plate 141, a ½-wave plate 142 and a polarizing plate 143. In this case, the order of the ¼-wave plate 141 and the ½-wave plate 142 may be reverse. The rotational angle of the ¼-wave plate 141, the ½-wave plate 142 and the polarizing plate 143 are set (rotation control) on the basis of the control signal from the polarization condition control part 241 shown in FIG. 1.

The line sensor 124 focuses the scattered light having the polarization state adjusted in the polarization analyzer 140 on a detection plane of the line sensor 124 to be detected. For example, TDI (Time Delay Integration) image sensor, time delay integration type image sensor, CCD (Charge Coupled Device) sensor and CMOS (Complementary Metal Oxide Semiconductor) sensor may be used. In this case, the position of the polarization analysis part 140 and the image forming lens 122 may be reverse.

The signal based on the scattered light detected thus is supplied to the signal processing and control part 250.

(Stage Part 170)

The stage part 170 includes an x-stage 170a, a y-stage 170b, a z-stage 170c and a θ-stage 170d.

The x-stage 170a is used to put thereon the semiconductor wafer 100 that is the sample to be inspected and having the surface on which minute pattern is formed and can be moved in x-direction.

The y-stage 170b, the z-stage 170c and the θ-stage 170d are also used to put thereon the semiconductor wafer 100 that is the sample to be inspected and having the surface on which minute pattern is formed and can be moved in y-direction, z-direction and θ-direction, respectively.

(Signal Processing and Control Part 250)

The signal processing and control part 250 includes an image processing part 200, an operation part 210, a control part 220, a polarization condition calculation part 240, polarization condition control part 241 and a height detection part 160.

The image processing part 200 performs signal processing to process images on the basis of the scattered light from the semiconductor wafer 100 detected by the line sensor 124.

Concretely, two images (an inspection image based on the scattered light in a predetermined area on the semiconductor wafer 100 and an image (image (reference image) obtained by photographing adjacent pattern or adjacent die) based on scattered light from an area adjacent to the predetermined area and expected to be the same image as the inspection image originally) are sent to the image processing part 200. The two images are compared to extract a defect candidate, so that judgment, classification and sizing of defect are performed from features such as distribution and intensity of scattered light of the extracted defect candidate.

Figure 5:
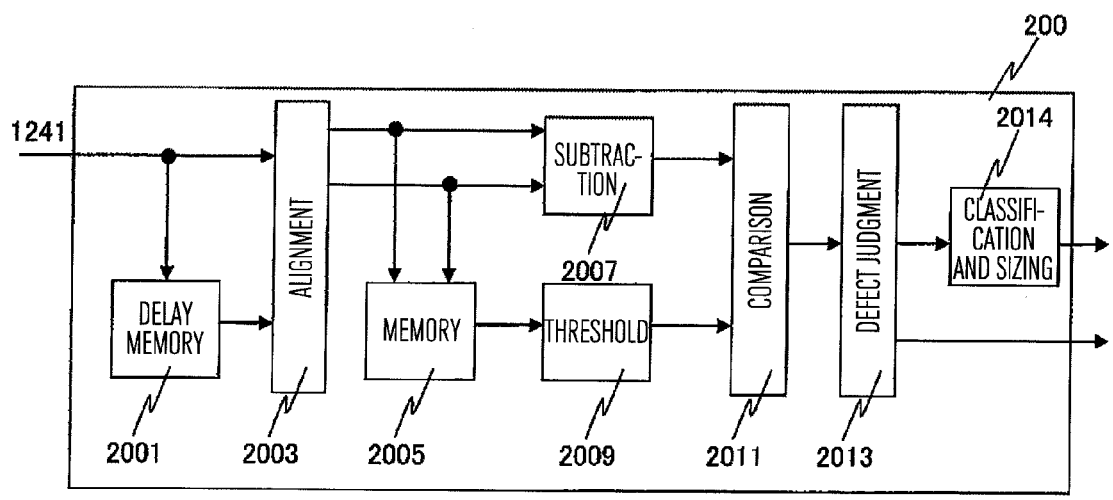
FIG. 5 is a block diagram schematically illustrating an image processing part in the first embodiment of the optical inspection apparatus according to the present invention.

FIG. 5 is a block diagram schematically illustrating the image processing part in the first embodiment of the optical inspection apparatus according to the present invention.

An image 1241 of an inspection die obtained by the line sensor 124 and an image of die obtained by the last inspection and recorded in a delay memory 2001 are aligned by an alignment part 2003 and its result is once stored in a memory 2005. Then, a subtraction part 2007 calculates (subtraction) a difference image between both the images. At this time, scattered light from a defect is different from scattered light from normal part and accordingly image having emphasized scattered light from defect can be obtained. Since normal part is dark and defective part is bright, the obtained difference image is compared with a threshold image stored in a threshold memory 2009 by a comparison part 2011 and a defect judgment part 2013 judges defect from the result obtained by the comparison part 2011. The threshold image stored in the threshold memory 2008 is decided from statistical brightness of plural normal parts.

The operation part 210 operates the apparatus.

The control part 220 controls each part of the apparatus. For example, the control part 220 receives detection result from the height detection part 160 described later, controls positions of the x-stage 170a, the y-stage 170b, the z-stage 170c and the θ-stage 170d of the stage part 170 and sends control signal to the spatial filter 123.

The polarization condition calculation part 240 calculates optimum polarization state in accordance with circuit pattern on the surface of the semiconductor wafer on the basis of the intensity of scattered light previously measured and detected and data of inspection conditions of the polarization generation part 130, the polarization analysis part 140 and the like and sends the calculated result to the polarization condition control part 241.

The polarization condition control part 241 sends the optimum polarization state received from the polarization condition calculation part 240 to the polarization generation part 130, the polarization analysis part 140 and the like and controls the polarization conditions.

The height detection part 160 detects the height of the stage part 170 in inspection and sends the detection result to the control part 220. When any shift or difference occurs in the height of stage, the shift or difference in the height of stage is corrected using a control signal from the control part 220 on the basis of the detection result of the height detection part.

Although detailed description is made later, in the present invention the polarization state of the scattered light from the repeat pattern on the semiconductor wafer depending on an incident direction and an elevation angle of the illumination optical system 110, a direction and an elevation angle of the detection optical system 120 and a numerical aperture (NA) of the object lens 121 are decided and conditions for suppressing the scattered light from the repeat pattern part most is derived by the polarization generation part 130 and the polarization analysis part 140, so that inspection is performed.

Figure 2:
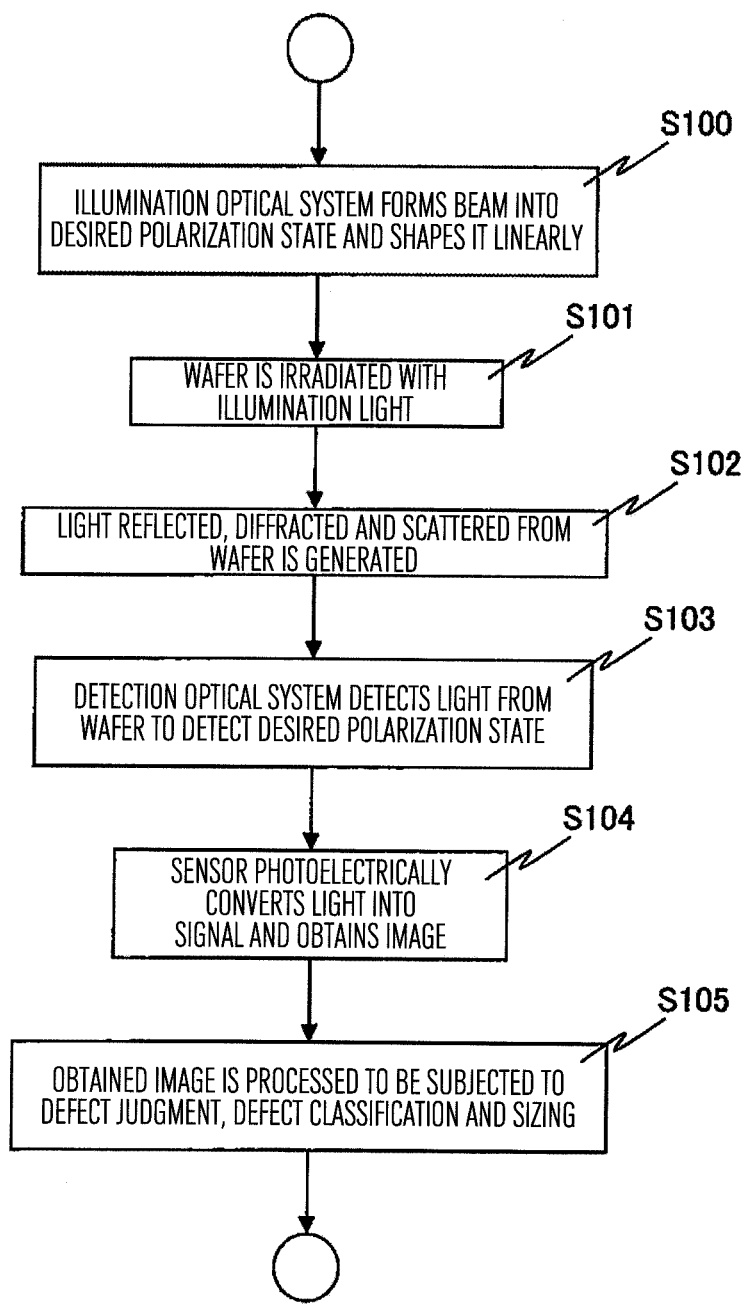
FIG. 2 is a flow chart showing the first embodiment of an optical inspection method according to the present invention.

FIG. 2 is a flow chart showing the first embodiment of the optical inspection method according to the present invention.

The illumination optical system 110 forms the beam into a desired polarization state and further shapes it linearly (S100) and irradiates the semiconductor wafer 100 being moved continuously in the x-direction by the x-stage 170a with the linearly shaped illumination light (S101). Light reflected, scattered and diffracted from the semiconductor wafer 100 in response to the irradiation of the illumination light shaped linearly (S102) is detected by the detection optical system 120 (S103) and an image is obtained from a signal converted photoelectrically by the line sensor 150 (S104). The obtained image is processed to be subjected to defect judgment, defect classification and sizing (S105).

Detailed operation contents of each step are now described.
(S100)

In S100, the laser beam emitted from the light source 111 of the illumination optical system 110 is shaped by the attenuation filter 112 and adjusted by the polarization generation part 130 so as to obtain the polarization state decided on the basis of the control signal from the polarization condition control part 240. Then, the light having the adjusted polarization state from the polarization generation part 130 is sent to the linear beam generation part 115, which generates a linear beam.
(S101)

In S101, the semiconductor wafer 100 is irradiated with the linear beam generated in S100.

At this time, in the optical dark-field inspection apparatus, the semiconductor wafer 100 is irradiated with the illumination light while the semiconductor wafer 100 is scanned (the semiconductor wafer 100 and the illumination and detection optical systems 110 and 120 are being moved continuously in one direction relatively).
(S102)

Reflected, scattered and diffracted light is generated from the semiconductor wafer 100 in response to the linear beam with which the semiconductor wafer 100 is irradiated in S101.
(S103)

The reflected, scattered and diffracted light generated in S102 is focused by the object lens 121 of the detection optical system 120 and part of the reflected, scattered and diffracted light focused by the object lens 121 from the surface of the semiconductor wafer 100 is shielded by means of the spatial filter 123. Then, the polarization state of scattered light which is not shielded by the spatial filter 123 and is transmitted by the image forming lens 122 is adjusted by the polarization analyzer 140.

(S104)

The scattered light having the polarization state adjusted in S103 is detected by the line sensor 124 to obtain the image about the surface of the semiconductor wafer 100.
(S105)

The image obtained in S104 is processed by the image processing part 200 of the signal processing and control system 250 to be subjected to defect judgment, defect classification and sizing.

The diffracted light from repeat pattern is now described in detail. In FIG. 1, in order to remove the diffracted light from normal repeat pattern (repeat pattern having no defect) which is an obstacle to detection of the scattered light from the defect, the illumination optical system 110 is installed in the direction of 45 degrees to the longitudinal direction of the linear beam.

Generally, the diffracted light is generated vertically to the pattern structure. The structure of the semiconductor wafer to be inspected has line pattern in main axial directions x and y of FIG. 1 in many cases. The diffracted light is generated vertically to the line pattern and accordingly the diffracted light is increased in y- and x-directions. The elevation angle of illumination and NA (Numerical Aperture) of the object lens 121 for detection can be set properly to configure the apparatus so that the diffracted light from the line pattern does not enter the detection system positioned above if possible. The diffracted light entered the object lens 121 is removed by the spatial filter 123. Further, in the repeat pattern part of the sub-wavelength structure to which attention is paid in the present invention, the pitch (period) of the repeat pattern and the diffraction angle (scattering angle) have the relation of inverse proportion and accordingly the diffracted light is diffracted to outside of NA of the object lens 121, so that only scattered light is detected.

In the embodiment, in order to suppress the signal from the repeat pattern part, the polarization state of the repeat pattern part is utilized. The repeat pattern of the sub-wavelength structure is utilized as a polarizing element like wire grid polarizer from its strong polarization state. The Inventors of this patent application have found that the scattered light from the repeat pattern part of the sub-wavelength structure has uniform polarization state in relatively broad scattering angle. This effect is utilized to set the polarization state of the illumination optical system 110 and the polarization state detected by the photographing optical system 120 properly, so that the scattered light from the repeat pattern part incident on NA of the object lens 121 can be suppressed greatly. In the apparatus of the embodiment shown in FIG. 1, the illumination polarization state of the illumination optical system 110 can be set to any state by the polarization generator 130 and the detection polarization state of the detection optical system 120 can be set to any state by the polarization analyzer 140.

In the embodiment, the defect inspecting apparatus having both of the polarization generator 130 and the polarization analyzer 140 has been described, although both of them are not necessarily needed and even when only any one of them is used, the scattered light from the repeat pattern part can be suppressed and the scattered light having reduced noise can be detected.

Further, the polarization generator 130 and the polarization analyzer 140 may not be used as occasion arises and the ¼-wave plate 131 and the ½-wave plate 132 or the ¼-wave plate 141, the ½-wave plate 142 and the polarizing plate 143 may be structured to be inserted and extracted under certain circumstances.

Figure 6:
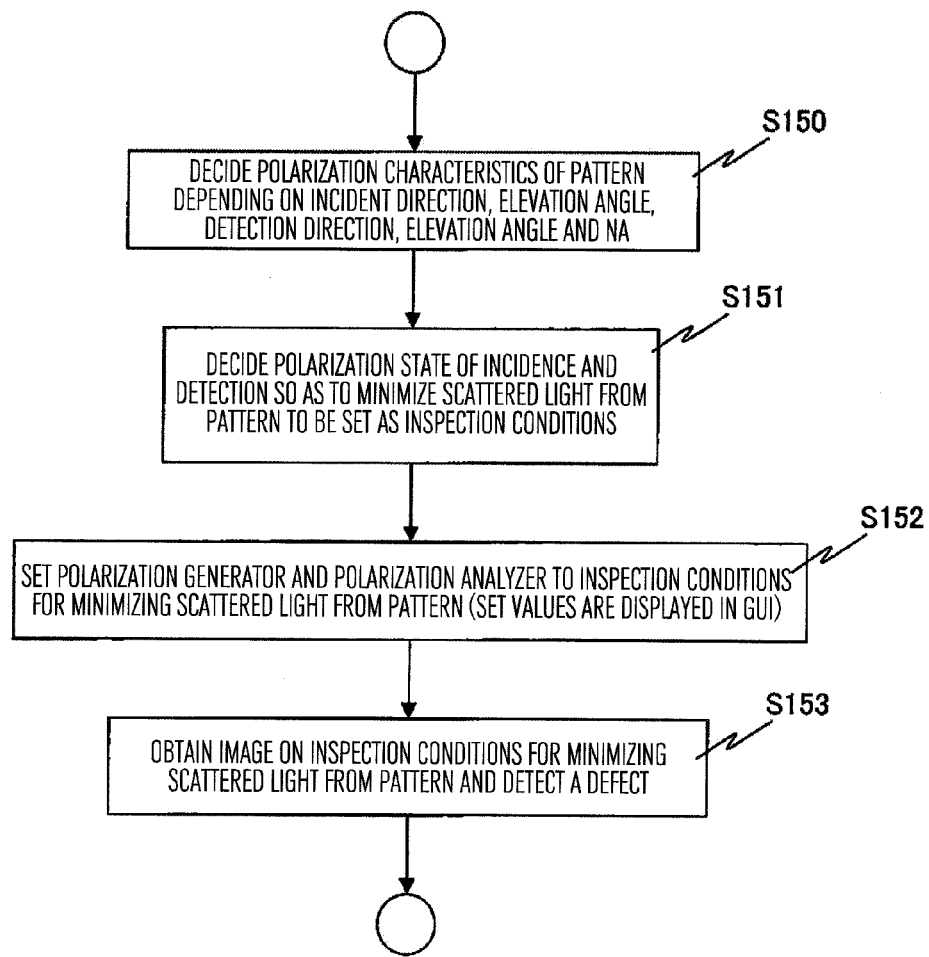
FIG. 6 is a flow chart of setting inspection conditions of the first embodiment of the optical inspection method according to the present invention.

FIG. 6 is a flow chart of setting inspection conditions of the first embodiment of the optical inspection method according to the present invention. The inspection conditions mean the polarization conditions (polarization state) of the polarization generation part 130 and the polarization analysis part 140 that minimize the scattered light from the repeat pattern in accordance with the repeat pattern form of the semiconductor wafer that is the object to be inspected. The polarization conditions of the polarization generation part 130 and the polarization analysis part 140 that minimize the scattered light from the repeat pattern are different depending on the repeat pattern form of the semiconductor wafer and accordingly optimum polarization conditions are required to be decided for each semiconductor wafer of the inspection object.

Figure 7:
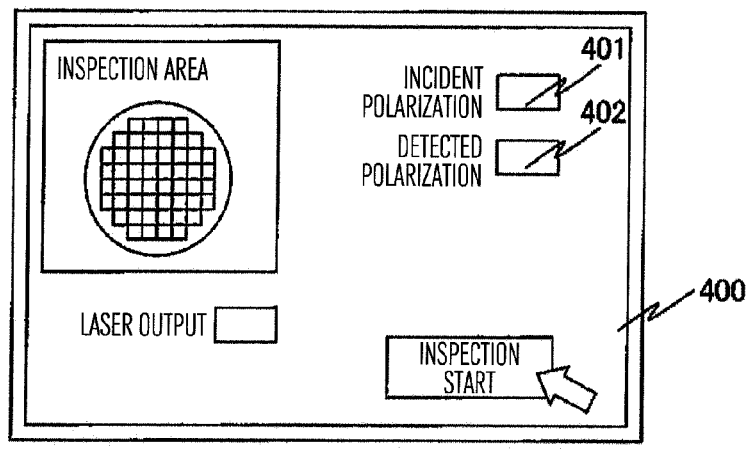
FIG. 7 is a schematic diagram illustrating a display unit of the first embodiment of the optical inspection apparatus according to the present invention.

In FIG. 6, the polarization state of the repeat pattern depending on the direction and the elevation angle of the illumination optical system 110, the direction and the elevation angle of the detection optical system 120 and NA of the object lens 121 are decided (S150) and the polarization state of incidence and detection is decided so as to minimize the scattered light from the repeat pattern to be set as the inspection conditions (S151). The polarization generator 130 and the polarization analyzer 240 are set to the inspection conditions for minimizing the scattered light from the repeat pattern. At this time, set values of the inspection conditions are displayed in GUI (S152) as shown in FIG. 7. Finally, image is obtained on the inspection conditions decided in S152 to minimize scattered light from repeat pattern to detect a defect (S153). At this time, the polarization state of a foreign matter or defect are different from those of scattered light from repeat pattern part and accordingly the foreign matter or the defect can be revealed.

Detailed operation contents of each step are now described.

(S150)

In S150, the polarization state of the repeat pattern part are decided. Generally, the polarization state of an object can be expressed by parameters of 16 elements of Mueller matrix (4×4 matrix) M. The intensity I of scattered light of the repeat pattern part can be expressed by the following expression by using Stokes vector S (4×1 vector) expressing the polarization state of illumination light generated by the polarization generator 130 and the first line Ma (1×4 vector) of Mueller matrix expressing the polarization state detected by the polarization analyzer 140.

$$I = Ma \cdot M \cdot S \quad \text{(MATH. 1)}$$

Here, S depends on the direction of the ¼-wave plate 131 and the ½-wave plate 132 constituting the polarization generator 130. Further, Ma depends on the direction of the ¼-wave plate 141, the ½-wave plate 142 and the polarizing plate 143 constituting the polarization analyzer 140. Accordingly, the polarization state of the repeat pattern part can be derived from the intensity of the scattered light of the repeat pattern part for 16 different combinations of the polarization generator 130 and the polarization analyzer 140 each having four kinds of combinations.

(S151)

The step (S151) of deciding the inspection conditions is now described. In the expression 1, when M is known, conditions of S and Ma can be given to calculate I. Here, S and Ma for minimizing the intensity of the scattered light from the repeat pattern part are calculated. Decision of S means that the polarization state generated by the polarization generator 130 is decided and decision of Ma means that the polarization state detected by the polarization analyzer 140 is decided. Since S and Ma each have 4 items, it is difficult to calculate I that is minimum. Accordingly, it is considered that the Levenberg-Marquardt method or the steepest descent method which is an optimization method for plural parameters is used, while these methods are not considered.

Concretely, the polarization conditions of the polarization generation part 130 and the polarization analysis part 140 are set to any values and the semiconductor wafer 100 is irradiated with illumination light using the illumination optical system 130. Reflected, diffracted and scattered light from the semiconductor wafer 100 is detected using the detection optical system 120. At this time, the intensity of the detected scattered light is I and the polarization conditions of the polarization generation part 130 and the polarization analysis part 140 correspond to S and Ma. In the embodiment, it is necessary to obtain 16 combinations of I, S and Ma. These values are used to calculate M, so that M becomes a known value and S and Ma optimum to inspection of the semiconductor wafer can be obtained.

(S152)

Next, the step (S152) of deciding the state of the polarization generator 130 that realizes the polarization state S and the state of the polarization analyzer 140 that realizes the polarization state Ma detected is described. S is the function of direction of the ¼-wave plate 131 and the ½-wave plate 132 constituting the polarization generator 130 and when the incidence polarization state to the polarization generator 130 and the polarization state S wanted to be realized are known, the direction of each element can be calculated back easily by calculation of the Mueller matrix expressing the polarization state of the ¼-wave plate 131 and the ½-wave plate 132. Similarly, Ma is the function of direction of the ¼-wave plate 141, the ½-wave plate 142 and the polarizing plate 143 constituting the polarization analyzer 140 and the direction of each element can be calculated back easily by calculation of the Mueller matrix. The directions of elements calculated thus are set as the inspection conditions.

(S153)

Finally, the semiconductor wafer is inspected on the inspection conditions calculated in S152 (S153). The scattered light from the normal repeat pattern part can be suppressed to thereby reveal the scattered light from foreign matter or defect and detect the foreign matter or defect with high sensitivity.

FIG. 7 is a schematic diagram illustrating the display unit of the first embodiment of the optical inspection apparatus according to the present invention.

For example, in the operation flow of setting the inspection conditions, the user can set the polarization state of the polarization generation part 130 and the polarization analysis part 140. Further, in the defect inspection flow, inspection can be made on the basis of the optimum polarization state of the polarization generation part 130 and the polarization analysis part 140 decided in the inspection condition setting flow and the user can known the polarization conditions on which inspection is being made.

In inspection, in order to inspect the whole surface of wafer, the stage is scanned in the x-direction and positions of the illumination optical system 110 and the semiconductor wafer are changed relatively.

FIG. 8 is a diagram showing changing state of inspection conditions to circuit pattern form on a sample. As shown in FIG. 8, when different repeat pattern parts having y-direction lines and space parts 301 and x-direction lines and space parts 302 are arranged in the scanning direction, respective polarization state can be previously derived and conditions of the polarization generator 130 and the polarization analyzer 140 can be switched from conditions A to conditions B at high speed, so that optimum inspection can be made in each repeat pattern part. Further, in the embodiment, rotation of the wave plates is used for control of polarization, although an electro-optics modulator or a magneto-optics modulator may be used.

Embodiment 2

The second embodiment is described with reference to FIGS. 9A, 9B and 10.

Figure 9A:
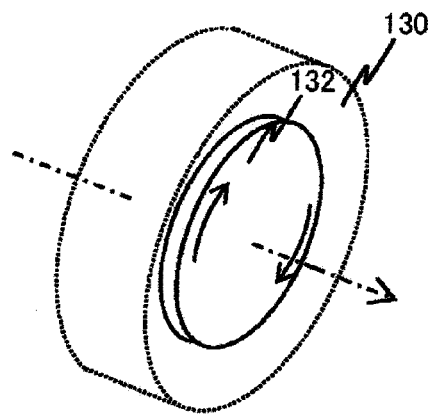
FIG. 9(a) is a schematic diagram illustrating a polarization generator of a second embodiment of the optical inspection apparatus according to the present invention.
Figure 9B:
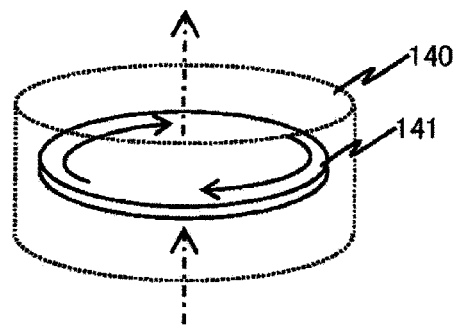
FIG. 9(b) is a schematic diagram illustrating a polarization analyzer of the second embodiment of the optical inspection apparatus according to the present invention.
Figure 10:
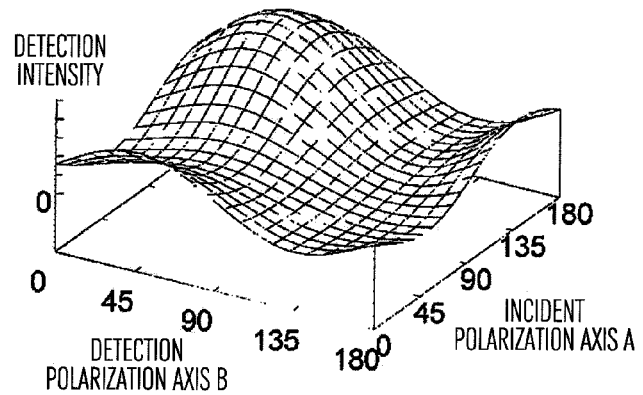
FIG. 10 is a diagram showing the relation of polarization axes of incident linear polarization and detection linear polarization and intensity of scattered light from repeat pattern part.

FIG. 9A is a diagram schematically illustrating the polarization generator of the second embodiment of the optical inspection apparatus according to the present invention and FIG. 9B is a diagram schematically illustrating the polarization analyzer of the second embodiment of the optical inspection apparatus according to the present invention. FIG. 10 is a diagram showing the relation of polarization axes of incident linear polarization and detection linear polarization and intensity of scattered light from repeat pattern part.

The embodiment 2 is different from the embodiment 1 in that polarization illumination that is illumination light is limited to linear polarization. Consequently, configuration of the polarization generator 130 and the polarization analyzer 140 is different from the embodiment 1. Here, only inspection condition setting flow shown in FIG. 6 that is different from the first embodiment is described in detail.

When linear polarization is incident, not only regular reflected light but also scattered light sometimes become uniform linear polarization in a relatively broad scattered angle depending on repeat pattern form of the semiconductor wafer. At this time, the polarization generator 130 and the polarization analyzer 140 are required to have configuration capable of treating only linear polarization and scattered light from the repeat pattern part to be inspected can be suppressed.

FIG. 9A schematically illustrates the polarization generator 130. When the light source 111 is a laser that emits linear polarization, the polarization generator 130 is composed of only the ½-wave plate 132 and the polarization axis of linear polarization of beam is controlled in accordance with the direction of the ½-wave plate 132.

Further, FIG. 9B schematically illustrates the polarization analyzer 140. Since only linear polarization is extracted, the polarization analyzer 140 is composed of only polarizing plate 143.

Similarly to the embodiment 1, the inspection conditions of the polarization generator 130 and the polarization analyzer 140 are decided in accordance with the operation flow of FIG. 6, although the polarization generator 130 and the polarization analyzer 140 are limited to linear polarization, so that the conditions can be set easily. In the step (S150) of deciding the polarization state of the repeat pattern part, the polarization state of an object can be generally expressed by parameters of 16 elements of Mueller matrix (4×4 matrix) M, although only 9 elements are required to be considered when response to only linear polarization is considered. Accordingly, the polarization state of the repeat pattern part can be derived from the intensity of scattered light from the repeat pattern part for 9 different combinations of the polarization generation device 130 and the polarization analyzer 140 each having three kinds of combinations.

In the case of linear polarization even in step (S151) of deciding the inspection conditions, Stokes vector S (4×1 vector) expressing the polarization state of expression 1 and the first line Ma (1×4 vector) of Mueller matrix expressing the polarization state detected by the polarization analyzer 140 are the functions of a direction A of incident linear polarization and the direction B of detection linear polarization, respectively, and accordingly the detection intensity I is the function of A and B. When the scattered light from repeat pattern is substantially linear polarization, the intensity is changed sinusoidally in response to change of A and B and is minimized at certain values of A and B to approach 0. The directions A and B having the minimum intensity I represent the polarization states of incidence and detection forming the inspection conditions.

In step (S152) of deciding the state of the polarization generator 130 that realizes the polarization state S and the state of the polarization analyzer 140 that realizes the polarization state Ma detected, the polarization generator 130 controls the direction of the ½-wave plate 132 and the polarization analyzer 140 controls the polarizing plate 143 so that desired incidence and detection directions A and B are realized. Finally, inspection is performed on the condition of (S152). The scattered light from normal repeat pattern part can be suppressed to thereby reveal the scattered light from a foreign matter or defect and detect the foreign matter or defect with high sensitivity.

Further, the polarization generator 130 may be the system of controlling rotation of the ¼-wave plate 131 and the ½-wave plate 132 of FIG. 3 similarly to the embodiment 1 in order to correct polarization change caused by optical element such as lens in the illumination optical system 110.

Embodiment 3

The third embodiment of the present invention is described. In the embodiment, in the step (S150) of deciding the polarization state of the repeat pattern part in the detection condition setting flow of FIG. 6, optical simulation result is used instead of actual measurement result. Electric field component of the scattered light from the repeat pattern part is calculated by optical simulation such as the rigorous coupled wave analysis (RCWA) and the finite-difference time-domain method (FDTD) to obtain the polarization state. At this time, simulation is performed on the same conditions as the measurement conditions shown in the embodiment 1.

Furthermore, when the shape of defect to be inspected is obvious, the polarization state of scattered light from defect can be also calculated using the optical simulation. When the polarization state of both of the repeat pattern part and the defect are understood, a ratio (S/I) of the intensity I of scattered light from repeat pattern part detected and the intensity S of scattered light from defect can be measured and inspection can be made on the condition of incidence and detection polarization states in which S/I is maximum, so that the sensitivity can be maximized.

When the optical simulation result is used to obtain the optimum polarization state, it is not necessary to actually measure the scattered light on plural experiment conditions beforehand and accordingly time required to calculate the optimum inspection conditions is shortened.

Moreover, a reference wafer having a defect of which position and size are known is used to actually measure scattered light and conditions of incidence and detection polarization conditions having maximum S/I can be calculated by matrix calculation as described in the embodiment 1.

Embodiment 4

The fourth embodiment of the present invention is described with reference to FIGS. 11 and 12.

Figure 11:
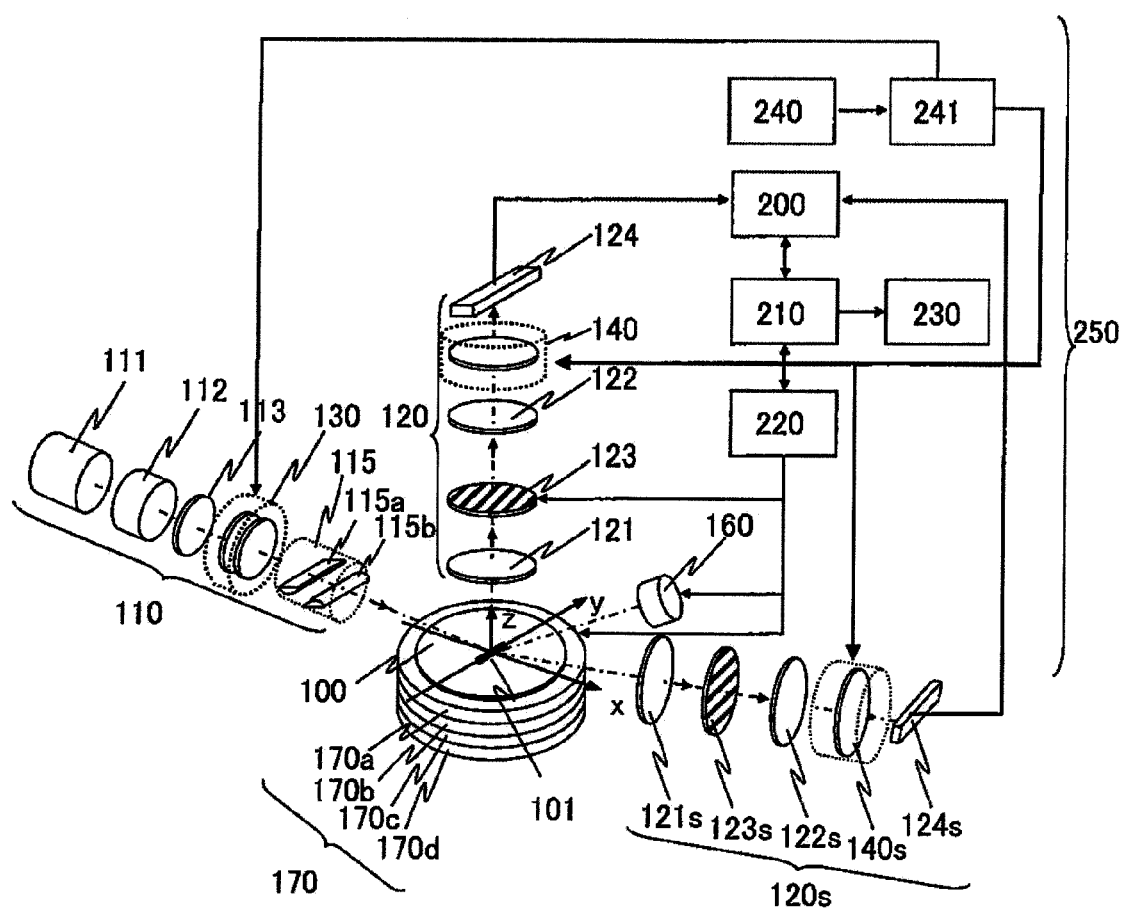
FIG. 11 is a schematic diagram illustrating an optical system of a fourth embodiment of an optical inspection apparatus according to the present invention.
Figure 12:
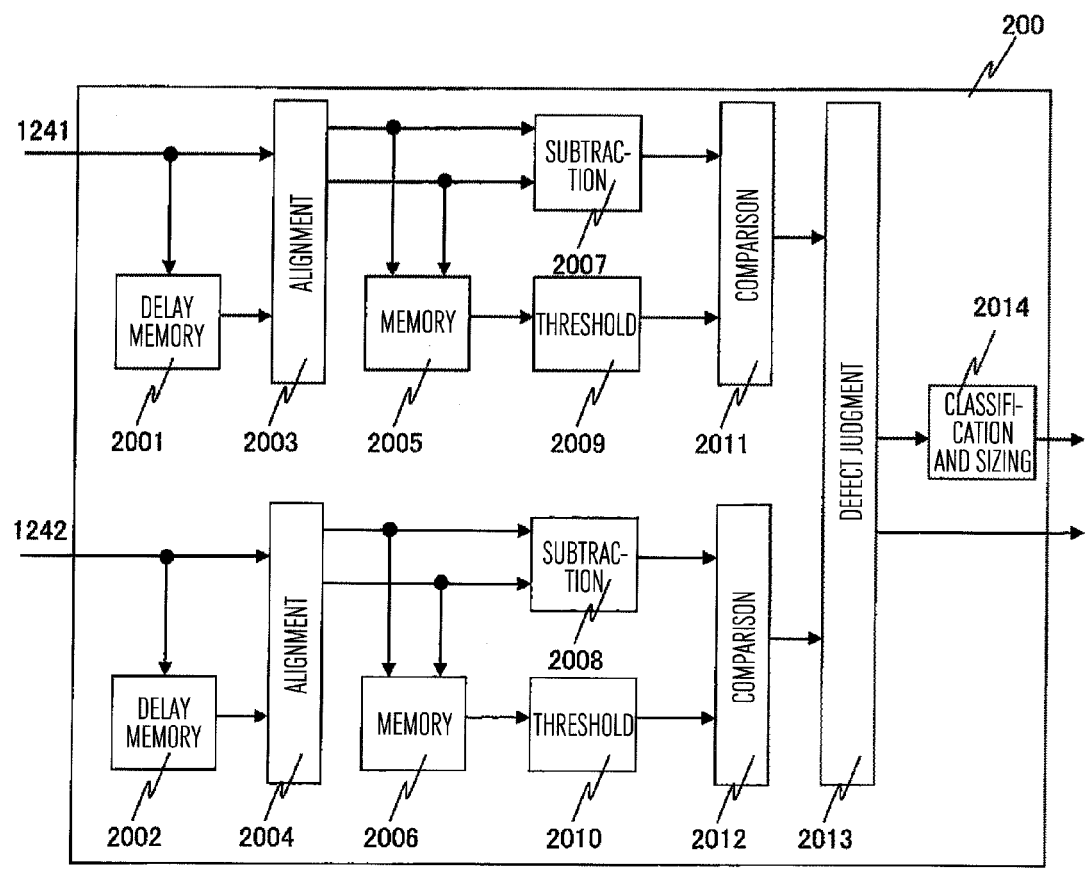
FIG. 12 is a block diagram schematically illustrating an image processing part in the fourth embodiment of the optical inspection apparatus according to the present invention.

FIG. 11 is a diagram schematically illustrating the optical system of the fourth embodiment of the optical inspection apparatus according to the present invention and FIG. 12 is a block diagram schematically illustrating an image processing part in the fourth embodiment of the optical inspection apparatus according to the present invention.

The configuration of the embodiment includes an oblique detection system 120S added to the configuration of the embodiment 1 shown in FIG. 1. Similarly to the upper detection system 120, the oblique detection system 120S includes an object lens 121S and an image forming lens 122S for focusing reflected, diffracted and scattered light from the semiconductor wafer 100 irradiated by the illumination optical system 110, a spatial filter 123S for removing diffracted light pattern produced by the repeat pattern part of semiconductor pattern, a polarization analysis part 140S composed of a polarizing plate and a wave plate and a line sensor 124 for detecting scattered light from wafer focused by the object lens 121S and the image-forming lens 122S.

In the embodiment, two detection optical systems 120 and 120S are provided for the illumination optical system 110. Accordingly, in optimization of inspection conditions, state of the illumination optical system 110 is fixed and the polarization conditions are decided so that scattered light from repeat pattern part is minimized in the detection optical systems 120 and 120S.

The image processing part 200 of FIG. 12 is described in detail. The dark-field optical inspection apparatus obtains a lot of images while the semiconductor wafer is scanned (while the semiconductor wafer 100 and the illumination and detection optical systems 110 and 120 are continuously moved in one direction relatively). As shown in FIG. 11, images 1241 and 1242 of inspection dies obtained by line sensors 124 and 124S and images of dies obtained by the last inspection and recorded in delay memories 2001 and 2002 are aligned by alignment parts 2003 and 2004 and results thereof are once stored in memories 2005 and 2006, so that difference image between the images is obtained by subtraction parts 2007 and 2008 (subtraction). At this time, scattered light from defect is different from scattered light from normal part and accordingly image having scattered light emphasized from defect can be obtained. Since dark image is obtained from normal part and bright image is obtained from defect part, difference images obtained are compared with threshold images stored in threshold memories 2009 and 2010 by comparison parts 2011 and 2012 and respective results obtained from comparison parts 2011 and 2012 are combined by defect judgment part 2013 to judge defect. The threshold images stored in the threshold memories 2009 and 2010 are decided from statistical brightness of normal part, for example.

Embodiment 5

The fifth embodiment of the present invention is described with reference to FIG. 13.

Figure 13:
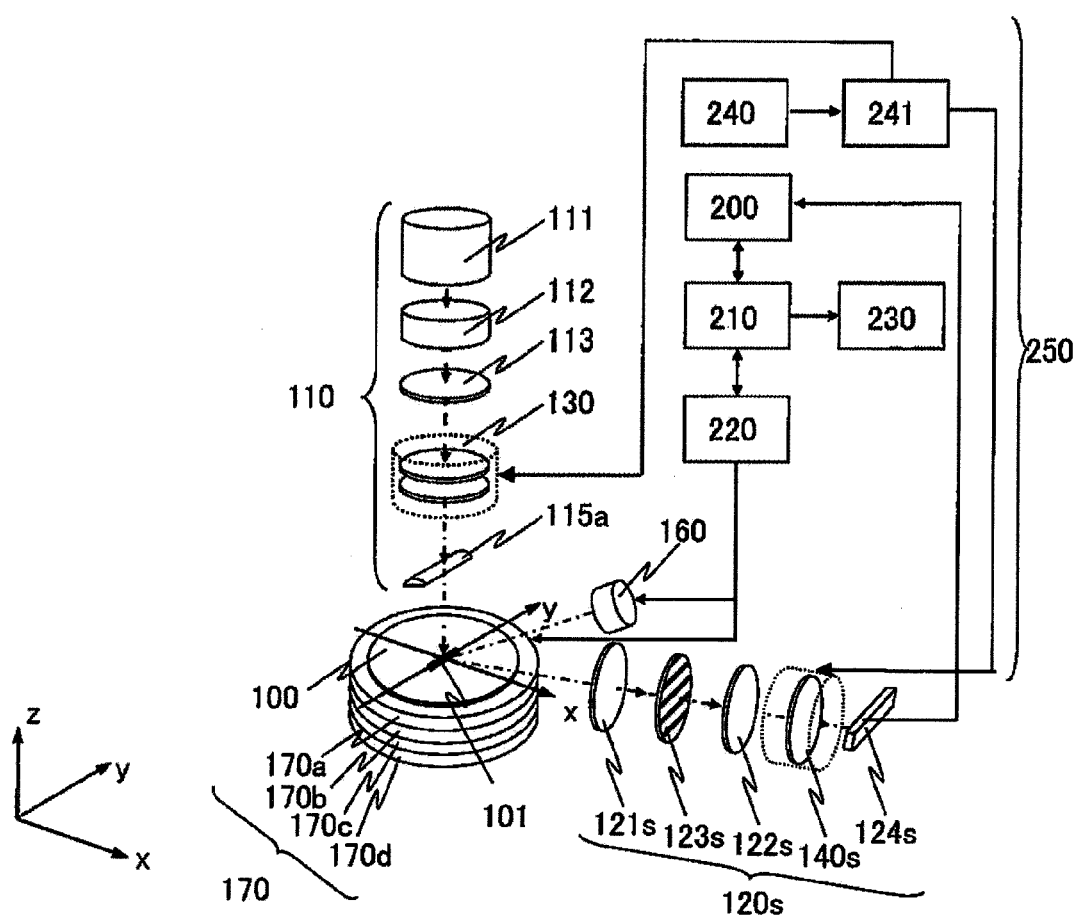
FIG. 13 is a schematic diagram illustrating an optical system of a fifth embodiment of an optical inspection apparatus according to the present invention.

FIG. 13 schematically illustrates an optical system of the fifth embodiment of the optical inspection apparatus according to the present invention.

The fifth embodiment is different from the first embodiment in that the illumination optical system 110 is structured to make epi-illumination to the wafer and the photographing optical system 120 is structured to be an oblique photographing system set in oblique direction to the wafer. The operation flows for inspection and image processing are the same as the embodiment 1.

In the embodiment, since the illumination optical system 110 makes downward illumination, illumination light reaches lower part of stereo-structure of the repeat pattern part and accordingly scattered light from a foreign matter or defect present in the lower part of the repeat pattern part can be detected stronger, so that the foreign matter or defect can be inspected with higher sensitivity. In other words, it is an object to detect stronger signal from a defect in a photographed image obtained by the line sensor 124 and suppress signal from the repeat pattern, so that detection sensitivity of defect can be improved.

In the foregoing, the present invention made by the Inventors has been described concretely on the basis of the embodiments, although it is needless to say that the present invention is not limited to the embodiments and various changes and modifications can be made without departing from the spirit and the scope of the invention.

REFERENCE SIGNS LIST

100 . . . wafer
101 . . . linear beam
110 . . . illumination optical system
111 . . . laser light source
112 . . . attenuation filter
113 . . . beam expander
115 . . . linear beam generation part
115a, 115b . . . cylindrical lens
120 . . . photographing optical system
121 . . . image forming lens
122 . . . object lens
123 . . . spatial filter
124 . . . TDI sensor
1241 . . . photographed image
130 . . . polarization generator
131 . . . ¼-wave plate
132 . . . ½-wave plate
140 . . . polarization analyzer
141 . . . ¼-wave plate
142 . . . ½-wave plate
143 . . . polarizing plate
160 . . . height detection part
170 . . . stage part
170a . . . x-stage
170b . . . y-stage
170c . . . z-stage
170d . . . θ-stage
200 . . . image processing part
210 . . . operation part
220 . . . control part
230 . . . display unit
250 . . . signal processing and control system
301 . . . x-direction line and space part
302 . . . y-direction line and space part
400 . . . monitor
401 . . . incident polarization
402 . . . detection polarization
2001, 2002 . . . delay memory
2003, 2004 . . . alignment part
2005, 2006 . . . memory
2007, 2008 . . . subtraction part
2009, 2010 . . . threshold memory
2011, 2012 . . . comparison part
2013 . . . defect judgment part
2014 . . . classification and sizing part

The invention claimed is:

1. A defect inspecting apparatus comprising:
an irradiation optical system including a light source to emit illumination light and a polarization generation part to adjust polarization state of the illumination light emitted from the light source;
a detection optical system including a polarization analysis part to adjust polarization state of scattered light from a sample irradiated by the irradiation optical system and a detection part to detect the scattered light adjusted by the polarization analysis part; and a signal processing system to process the scattered light detected by the detection optical system to detect a defect presenting in the sample;

the polarization generation part adjusting the polarization state of the illumination light emitted from the light source on the basis of predetermined illumination conditions;

the polarization analysis part adjusting the polarization state of the illumination light emitted from the light source on the basis of predetermined detection conditions.

2. A defect inspecting apparatus according to claim 1, wherein the polarization generation part includes a ½-wave plate and a ¼-wave plate, and the polarization analysis part includes a ½-wave plate, a ¼-wave plate and a polarizing plate.

3. A defect inspecting apparatus according to claim 1, wherein the signal processing part includes a polarization condition control part to control polarization conditions of the polarization generation part and the polarization analysis part, and the polarization generation part and the polarization analysis part adjust the polarization state on the basis of a control signal from the polarization condition control part.

4. A defect inspecting apparatus according to claim 1, wherein the signal processing part includes a polarization condition calculation part to calculate polarization conditions of the polarization generation part and the polarization analysis part on the basis of actually measured result of the scattered light from the surface of the sample.

5. A defect inspecting apparatus according to claim 4, wherein the polarization condition calculation part calculates the polarization conditions for minimizing intensity of the scattered light from circuit pattern on the surface of the sample on the basis of the actually measured result.

6. A defect inspecting apparatus according to claim 1, wherein the signal processing part includes a polarization condition calculation part to calculate polarization conditions of the polarization generation part and the polarization analysis part on the basis of optical simulation result about the scattered light from the surface of the sample.

7. A defect inspecting apparatus according to claim 1, wherein the illumination optical system irradiates the surface of the sample with the illumination light in a vertical direction.

8. A defect inspecting method comprising:

an irradiation step of adjusting polarization state of illumination light emitted and irradiating a sample to be inspected with the illumination light;

a detection step of adjusting polarization state of scattered light from the sample irradiated in the irradiation step to be detected; and a signal processing step of processing the scattered light detected in the detection step and detecting a defect presenting in the sample;

in the irradiation step, the polarization state of the illumination light emitted on the basis of predetermined illumination conditions being adjusted;

in the detection step, the polarization state of the illumination light emitted on the basis of predetermined detection conditions being adjusted.

9. A defect inspecting method according to claim 8, wherein in the irradiation step, the polarization state of the illumination light emitted on the basis of the predetermined illumination conditions are adjusted by a ½-wave plate and a ¼-wave plate, and in the detection step, the polarization state of the illumination light emitted on the basis of the predetermined detection conditions are adjusted by a ½-wave plate and a ¼-wave plate.

10. A defect inspecting method according to claim 8, wherein the signal processing step includes a polarization condition control step of controlling polarization conditions adjusted in the irradiation step and the detection step, and the signal processing step adjusts the polarization state on the basis of the control in the polarization condition control step.

11. A defect inspecting method according to claim 8, wherein the signal processing step includes a polarization condition calculation step of calculating polarization conditions on the basis of actually measured result of the scattered light from the surface of the sample.

12. A defect inspecting method according to claim 11, wherein the polarization condition calculation step calculates the polarization conditions for minimizing intensity of the scattered light from circuit pattern on the surface of the sample on the basis of the actually measured result.

13. A defect inspecting method according to claim 8, wherein the signal processing step includes a polarization condition calculation step of calculating polarization conditions of the illumination step and the detection step on the basis of optical simulation result about the scattered light from the surface of the sample.

14. A defect inspecting method according to claim 8, wherein the illumination step irradiates the surface of the sample with the illumination light in a vertical direction.

* * * * *